United States Patent [19]

Schonbaum

[11] Patent Number: 4,645,661
[45] Date of Patent: Feb. 24, 1987

[54] METHOD FOR ALLEVIATING CISPLATIN-INDUCED NEPHROTOXICITY AND DITHIOCARBAMATE COMPOUNDS FOR EFFECTING SAME

[75] Inventor: Gregory R. Schonbaum, Memphis, Tenn.

[73] Assignee: St. Jude Children's Research Hospital, Memphis, Tenn.

[21] Appl. No.: 625,961

[22] Filed: Jun. 29, 1984

[51] Int. Cl.$^4$ ...... A61K 49/00; C07D 207/00/207/18; C07D 207/06
[52] U.S. Cl. .................................. 424/10; 548/403; 548/565; 548/579; 546/263; 546/189; 514/476; 514/483; 514/332; 514/316; 514/422; 558/235; 558/236; 558/237; 558/238
[58] Field of Search .................. 260/455 A; 424/300, 424/10; 548/403, 565, 579; 546/263, 189; 514/476, 483, 332, 316, 422; 558/235, 236, 237, 238

[56] References Cited

U.S. PATENT DOCUMENTS

| | | | |
|---|---|---|---|
| 3,051,625 | 8/1962 | Rao | 260/455 A |
| 4,177,263 | 12/1979 | Rosenburg et al. | 260/455 A |
| 4,310,515 | 1/1982 | Granatek et al. | 260/455 A |
| 4,339,437 | 7/1982 | Rosenberg et al. | 260/455 A |

FOREIGN PATENT DOCUMENTS

| | | | |
|---|---|---|---|
| 2318020 | 11/1973 | Fed. Rep. of Germany | 260/455 A |
| 2329485 | 12/1973 | Fed. Rep. of Germany | 260/455 A |
| 1314392 | 4/1973 | United Kingdom | 260/455 A |

OTHER PUBLICATIONS

Morrison et al., Organic Chemistry, Third Edition, New York University, pp. 327–328.
Elliott, W. C., et al., Cancer Research, 43: 3759–3762 (1983).
Jones, S. G., et al., Research Communications in Chemical Pathology and Pharmacology, 40: 155–163 (1983).
Gale, G. R., et al., Ibid., 41: 293–302 (1983).

Primary Examiner—Henry R. Jilan
Assistant Examiner—Robert C. Whittenbaugh
Attorney, Agent, or Firm—Saidman, Sterne, Kessler & Goldstein

[57] ABSTRACT

A method for alleviating cisplatin compound-induced nephrotoxicity in animals comprising administering to the animal an effective amount of a polar dithiocarbamate compound. The polar dithiocarbamate compounds have the formula:

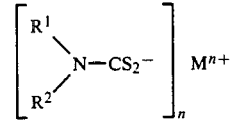

In the above formula, $R^1$ and $R^2$ are hydrocarbon groups and $R^1$, $R^2$, or both $R^1$ and $R^2$ contain a polar group substituted thereon. M is a pharmaceutically acceptable cation and n is an integer of from 1 to 3.

Novel polar dithiocarbamate compounds are disclosed as well.

10 Claims, 1 Drawing Figure

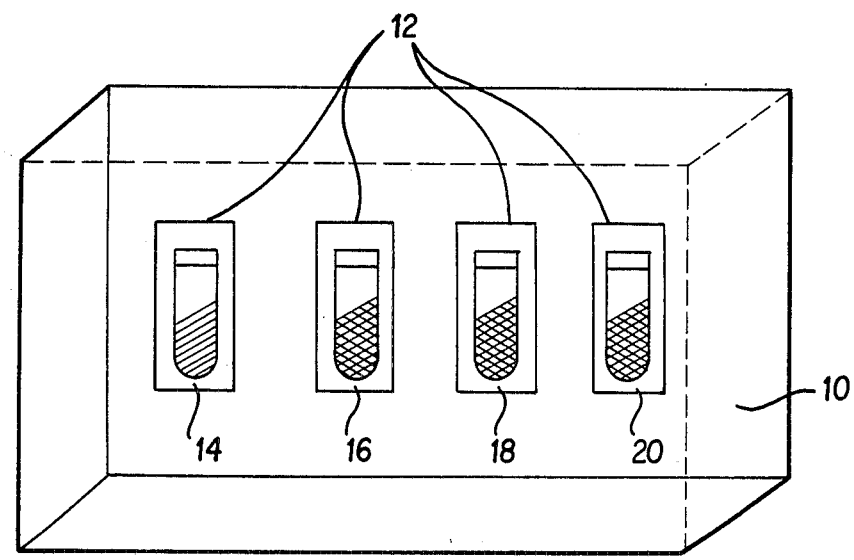

METHOD FOR ALLEVIATING CISPLATIN-INDUCED NEPHROTOXICITY AND DITHIOCARBAMATE COMPOUNDS FOR EFFECTING SAME

BACKGROUND OF THE INVENTION

The present invention was partly made using funds from the United States Government. The Government has certain rights in this invention.

1. Field of the Invention

The present invention relates generally to a method for alleviating cisplatin-induced nephrotoxicity. More specifically, the invention is directed to the discovery that administration of polar dithiocarbamate (PDC) compounds provides effective protection against the toxic effects normally associated with cisplatin and its analogues. A further aspect of this invention includes novel polar dithiocarbamate compounds as well.

2. Brief Description of the Prior Art

Cisplatin and its analogues (also referred to in this application as cisplatin compounds) are a unique group of compounds in the antineoplastic group of agents. They were first noted to have an antibiotic effect in 1965 and have since been found to be potent antitumor agents in animals.

Structurally, the compounds represent a complex formed by a central atom of platinum and surrounded by various arrangements of chlorine atoms or ammonia groups in a cis-planar relationship. Cisplatin and typical analogues thereof are described in U.S. Pat. No. 4,177,263 to Rosenberg et al., U.S. Pat. No. 4,310,515 to Granateck et al., U.S. Pat. No. 4,339,437 to Rosenberg et al., German Pat. No. 2,318,020 to Rustenberg, and German Pat. No. 2,329,485 to Research Corporation.

Cisplatin and its analogues have become widely used in the chemotherapy of a variety of human malignancies and have been found to be especially active in the treatment of testicular, head and neck, thyroid, bladder, ovarian, and endometrial cancers. However, the use of these compounds is limited by their side effects, particularly nephrotoxicity. Many patients develop evidence of both renal tubular dysfunction and depression of glomerular filtration rate, as indexed by serum creatinine. Further, the recovery of renal function is often incomplete after higher doses or repeated courses of cisplatin therapy. While renal pathology with functional impairment is the main toxic complication of cisplatin therapy, other sites of toxicity in human patients include the gastrointestinal system, inner ear, bone marrow, and nervous system.

Cisplatin and its analogues appear to be directly toxic to the renal tubules, usually most severe in the proximal tubules, but tubule toxicity may also be observed in the distal tubules and collecting ducts as well. Long term cisplatin therapy in patients produces regular and persistent decreases in the glomerular filtration rate, recovery from which does not appear to occur.

A three point hypothesis to explain the nephrotoxicity of cisplatin has been suggested: (1) cisplatin is a direct tubular toxin; (2) the agent must be present in tubular urine at minimal concentrations for a minimum period of time (minutes) for damage to occur; and (3) one theory regarding its biochemical mechanism of toxicity is mediation via inhibition of ATPase activity. Accordingly, a variety of methods for reducing the nephrotoxicity of cisplatin have been proposed.

Included among the proposed methods are hydration and osmotic diuresis, pharmacological diuretics, or chelating agents. Among the compounds proposed for treatment of nephrotoxicity induced by cisplatin are penicillamine, probenecid, superoxide dismutase, S-2-(3-amino-propylamino)-ethylphosphorothioic acid, thiourea, thiosulfate, and sodium diethyldithiocarbamate (DDTC).

DDTC administered following cis-diamminedichloroplatinum(II) (DDP) has been reported to attenuate structural renal damage and elevation of blood urea nitrogen (BUN) in rats. However, as reported by Elliott et al., *Cancer Research,* 43:3769–3762, August 1983, while DDTC rescue attenuated some structural DDP injury in the animal model, DDP-mediated proximal tubular dysfunction was only marginally attenuated by DDTC and glomerular filtration rate, as indexed by serum creatinine, was not protected at all.

Additionally, two recent articles: one by Jones et al., *Res. Comm. Chem. Pathol. Pharmacol.* 40:155 (1983), the other by Gale et al., Ibid. 41:293 (1983), each report on the effectiveness of a single polar dithiocarbamate compound, respectively ammonium N,N-(2-hydroxyethyl)-dithiocarbamate and sodium N,N-(2-hydroxyethyl)dithiocarbamate, for treatment of heavy metal poisoning wherein the metal is cadmium. The references contain no disclosure directed to the use of the compounds for attenuation of cisplatin toxicity.

Thus a need has continued to exist for the development of a method for alleviating cisplatin-induced nephrotoxicity. The well-recognized anti-neoplastic characteristics of cisplatin and its analogues make these compounds extremely valuable for treatment in cancer patients. However, they are dose-limited by their nephrotoxic characteristics.

SUMMARY OF THE INVENTION

Cisplatin therapy has proven to have substantial chemotherapeutic value and is employed in the treatment of a variety of neoplastic conditions. However, due to the inherent toxicity of the compounds, particularly with regard to renal function, the compounds are dose-limited.

Faced with the almost ever-present dichotomy of chemotherapy wherein the very drug which is therapeutically effective against the cancer is also toxic to the animal being treated, the present inventor set out to develop a method for alleviating the toxic side effects associated with cisplatin therapy. This endeavor has resulted in a method of treatment, and certain novel compounds for effecting same, wherein polar dithiocarbamate compounds having the general formula

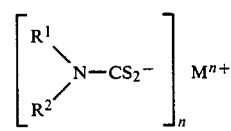

are administered to alleviate the toxic effects of cisplatin and its analogues.

In the above formula, $R^1$ and $R^2$ are hydrocarbon radicals, at least one of $R^1$ and $R^2$ being substituted with a polar group. M is a pharmaceutically acceptable cation and n is an integer of from one to three.

BRIEF DESCRIPTION OF THE DRAWING

The FIGURE is a top plan view of a kit for administering cisplatin and an effective amount of a polar dithiocarbamate.

DESCRIPTION OF THE PREFERRED EMBODIMENTS

In the instant invention, the term "alleviating" is meant to include reducing, preventing, and reversing the nephrotoxic effects of cisplatin and analogues thereof. As such, it encompasses those situations wherein renal toxicity is completely avoided as well as partially or completely eliminated. Thus, methods of the instant invention include those situations where administration of an effective amount of a polar dithiocarbamate compound (PDC) serves to reverse toxicity already having occurred, as well as to those situations where prophylactic methodology is involved.

The term "cisplatin and its analogues" includes the complex compounds of platinum (II) which may be organic, inorganic, or mixed. Organic complexes are most conveniently prepared by the reaction of a platinum salt with polyfunctional organic compounds such as beta-diketones, alpha-amino acids, alpha-hydroxy acids, and others usually designated as chelating agents. Platinum ion is incorporated into the chelating agents to form coordination compounds or chelates. Inorganic compounds of platinum useful in practicing the method of the present invention may be neutral, positively, or negatively charged. Platinum (II) forms $dsp^2$ complexes which are planar. Coordination compounds of platinum wherein the donor groups or ligands are Cl, Br, CN, $NO_3$, $NH_3$, ethylenediamine, propylenediamine, $H_2O$, OH, and OR (where R is lower alkyl) are representative. Cisplatin, cis-diamminedichloride platinum (II), is frequently used. Typical cisplatin compounds and their preparations are disclosed in U.S. Pat. Nos. 4,177,263, 4,310,515 and 4,339,437, the disclosures of which are incorporated by reference herein.

The term "cisplatin induced" includes nephrotoxicity resulting from administration of cisplatin or any analogue thereof as a part of active anticancer therapy as well as nephrotoxicity resulting from inadvertent ingestion of cisplatin or an analogue thereof, as well as any other manner by which the compounds are introduced into the body.

The term "animal" is meant to include any and all animals which experience nephrotoxicity as the result of the introduction of cisplatin or an analogue thereof into the system thereof. The method and compounds for practicing the method find particular utility for animals of the Class Mammalia and are especially useful in the treatment of primates, such as humans.

The term "administering" includes any and all means by which an effective amount of the active agent can be introduced into the system of the animal to be treated. Such methods include oral administration as well as administration parenterally, the active ingredient dissolved in or compounded with a suitable pharmaceutical carrier. The compounds can be employed in dosage forms such as tablets, capsules, powder packets, or liquid solutions, supensions or elixirs if used for oral administration. Sterile liquid formulations such as suspensions or solutions can be prepared for parenteral use. In such compositions the active ingredient will normally be present in an amount of at least 0.5% by weight based on the weight of the composition and up to 99.5% by weight thereof. Intravenous and intraperitoneal injections are the preferred methods of introducing the PDC compounds.

The compound may be administered prior to, simultaneous with, or shortly after the administration of cisplatin or an analogue thereof, but within two hours of cisplatin or cisplatin analogue treatment. A preferred regimen for introducing the PDC involves a split-regimen introduction wherein a part of the active ingredient is introduced prior to introduction of the cisplatin compound, followed by administration of a subsequent portion or portions thereafter. A typical method involves administration of a total dosage, for example, of 80 mg/kg, divided such that 40 mg/kg is introduced 0.5 minutes prior to introduction of cisplatin, followed by 20 mg/kg at 10 minutes post-cisplatin introduction and a second 20 mg/kg dose at 20 minutes post-cisplatin introduction. It is also within the contemplation of the present invention to administer the PDC component as a continuous infusion, typically over a one to three hour time period which coincides with the administration of the cisplatin compound.

The term "an effective amount of" includes any and all amounts of active ingredient (PDC) effective in alleviating cisplatin-induced nephrotoxicity in animals. Typically, the PDC is introduced in a total dosage in the range of 0.05–500 mg/kg, with a range of 5–400 mg/kg representing a more preferred range.

By "nephrotoxicity" is meant any and all physiological conditions which impair the ability of the kidney to perform its required function. As such, the term includes renal changes such as hydropic degeneration of proximal tubules, loss of brush border microvilli, diorganization, necrosis, and mineralization of tubular epithelial cells, appearance of granular casts within the lumina, cystic dilation of renal tubules in the other medulla, mineralization, hyperplagia, and atrophy of tubular epithelium in the outer stripe, atrophy of cortical tubules, increased BUN levels, decreased GFR uremia, and renal failure.

The polar dithiocarbamates (PDC) of the instant invention are those compounds which are stable, non-toxic, and form water-soluble non-toxic derivatives of platinum (II) which are readily eliminated. They include those compounds having the general formula:

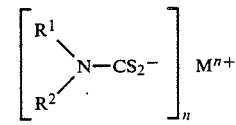

where $R^1$ and $R^2$ are aliphatic, alicyclic, or aromatic groups, or $R^1$ and $R^2$ taken together with the nitrogen atom, form a heterocyclic ring, and either $R^1$, $R^2$, both $R^1$ and $R^2$, or the heterocyclic ring contains at least one polar group.

Typical aliphatic groups include branched or straight chain alkyl groups having 1–8 carbon atoms, with 1–4 carbon atoms preferred. By alicyclic groups are meant those carbocyclic compounds having aliphatic properties. These include the saturated alicyclic hydrocarbons known as cycloparaffins as well as those compounds obtained by partial hydrogenation of aromatic rings. In general these groups contain three to eight carbon atoms.

The term "aromatic groups" includes those compounds having the characteristic chemical properties of benzene. Typically the aromatic groups are completely unsaturated and contain at least five or six carbon atoms.

Included among the groups wherein $R^1$ and $R^2$ are taken together with nitrogen to form a heterocyclic ring are the 5- and 6-membered rings. Such groups include pyrrole, pyrroline, pyrrolidine, pyridine, piperidine, and their derivatives.

By "polar group" are meant those groups whose monodithiocarbamate-platinum (II) derivatives and bis-dithiocarbamate-platinum (II) derivatives form metallo complexes having a water solubility of at least 0.1 micromole per ml. Typical polar groups include, but are not limited to, Cl, Br, I, F, $HSO_3$, $HCO_3$, $NO_2$, $NO_3$, $SO_3^-$, $CO_2^-$, $PO_3^{-2}$, $PO_2(OH)^-$, $PO_4^{-2}$, $PO_3(OH)^-$, $OR^3$, $N(R^3)_2$, and $CON(R^3)_2$, where $R^3$ is hydrogen or a group which will not eliminate the aqueous solubility of the platinum (II)-dithiocarbamate complex, such groups including lower alkyl and alkyl substituted with polar groups.

The particular carbon atom which contains the polar group is not significant, all substituted groups providing the required metallo complex water solubility being within the scope of the invention, provided that the substituent does not inferfere with the integrity of the chelating group or the aqueous solubility of metallo complexes. Thus, for example, where $R_1$ is a 5-carbon alkyl, the substitution may occur at any of the carbons in the alkyl group, with the above proviso.

M is a pharmaceutically acceptable cation. Typical pharmaceutically acceptable cations include alkali metals, alkaline earth metals, ammonium, and compounds having the general formula $NR^4R^5R^6$ wherein $R^4$, $R^5$ and $R^6$ are the same or different and include hydrogen or alkyl groups having one to four carbon atoms. Among the pharmaceutically acceptable cations, the alkali metal cations are the preferred ones, with sodium being the most preferred alkali metal cation.

n is an integer of one to three.

Sodium N,N-(2-hydroxyethyl)-dithiocarbamate, sodium N-methyl-N-(2-sulfoethyl)-dithiocarbamate, and sodium N-methyl-(2-carboxyethyl)-dithiocarbamate are among the preferred polar dithiocarbamate compounds. Among these compounds, the N,N-(2-hydroxyethyl)-dithiocarbamate is most preferred.

As mentioned above, sodium diethyldithiocarbamate (DDTC) is known to the prior art as having specific pharmacologic utility for cisplatin therapy rescue. However, the platinum chelate which forms when DDTC is used in adjunct chelation therapy for cisplatin-induced nephrotoxicity is highly insoluble and is only very slowly eliminated from the body. In contrast to DDTC, the polar dithiocarbamates of the instant invention are largely confined to the extracellular fluid, form water-soluble complexes with platinum, rapidly clear the plasma, and accumulate in the urine. Typical water solubilities for the PDC-platinum complexes are in the range of at least 0.2 micromoles per ml.

For example, solubilities at 37° C. in 0.02M phosphate buffer at a pH of 7.7 were determined for two dithiocarbamate-platinum(II) chelates having the general formula:

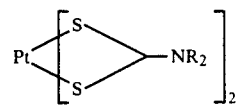

where R in this formula is $CH_3CH_2-$ (DDTC), the complex has a solubility of $0.0021 \times 10^{-4}$ M/L. In contrast, where R is $HOCH_2CH_2-$ (HED), the complex has a solubility of $2.1 \times 10^{-4}$ M/L, or a solubility of $10^3$ times that of the DDTC complex.

Further, the compounds have a therapeutic index substantially higher than that of DDTC, permitting much smaller amounts of the compounds to be used. For example, sodium N,N-(2-hydroxyethyl)-dithiocarbamate has a therapeutic index (the ratio of $LD_{50}$ to curative amount) of at least 20 while DDTC has a therapeutic index of 2–4.

The dithiocarbamate compounds of the instant invention are generally synthesized using techniques known to the art. Typical dithiocarbamate syntheses are disclosed in *The Dithiocarbamates and Related Compounds,* G. D. Thorn and R. A. Ludwig, Elsevier Publishing Company, Amsterdam/N.Y., 1962, pp. 7–41, incorporated by reference herein.

Generally, the parent compound, dithiocarbamic acid is obtained from its ammonium salt by treatment with cold acid. N-substituted dithiocarbamic acids are formed as their substituted ammonium salts by reaction of $CS_2$ with a secondary amine, usually in alcoholic or aqueous solution. It is common practice to use an alkali metal hydroxide to form the salt, according to the equation:

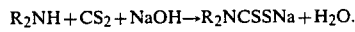

$$R_2NH + CS_2 + NaOH \rightarrow R_2NCSSNa + H_2O.$$

Having generally described the invention, a better understanding can be obtained by reference to certain specific preliminary examples, which are provided herein for purposes of illustration only and are not intended to be limiting unless otherwise specified.

EXAMPLE 1

The following is a synthesis of sodium N-methyl-N-(2-sulfoethyl)-dithiocarbamate (SEM) according to the equation:

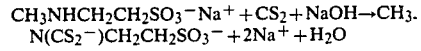

$$CH_3NHCH_2CH_2SO_3^-Na^+ + CS_2 + NaOH \rightarrow CH_3\text{-}N(CS_2^-)CH_2CH_2SO_3^- + 2Na^+ + H_2O$$

To a suspension of nitrogen saturated carbon disulfide (3.9 gm, 51 mmol) and sodium 2-(methylamino)ethane sulfonate (8.05 gm, 50 mmol in 40 ml oxygen-free water), in a closed system reactor, was added, with vigorous stirring, 50 mmol of deoxygenated sodium hydroxide solution (10 ml, 5M) at such a rate (0.3 to 0.5 ml/min) that the temperature did not exceed 20°–25° C. Stirring was continued until the reaction mixture became homogenous (approx. 0.5 hr). The reaction product was recovered and lyophilized. The yield was 95%±3%.

The lyophilized product was recrystallized by addition of a solution containing 1 gm of crude SEM-dissolved in 1.5 ml of nitrogen saturated agueous sodium hydroxide-to 15 ml of absolute ethanol at 45° C. A second portion of absolute ethanol was then added dropwise, with removal of any precipitate that formed at 45° C. by filtration, using Whatman No. 1 filter paper. The temperature was maintained at 45° C.±5° C. This solution was then crystallized by cooling to 20° C. The crystals were collected on a Buchner funnel, washed with cold absolute ethanol and dried in a vacuum dessicator at partial pressure of approximately 20 mm Hg.

EXAMPLE 2

Sodium N,N-(2-hydroxyethyl)-dithiocarbamate (HED) was tested in Fisher 344 rats bearing Walker 256 carcinosarcoma, at the total dosage of 80 mg/kg using a split-dose regimen. 40 mg/kg was administered intravenously 0.5 minutes prior to cisplatin therapy (6 mg/kg IV). Ten minutes following cisplatin administration, 20 mg/kg of HED was administered intraperitoneally, followed by a second 20 mg/kg dose, also administered intraperitoneally, 10 minutes after the first intraperitoneal administration. By this regimen, HED maintained BUN at 17.7±1.7 mg/dl, limited elevation in urine N-acetyl-beta-glucose aminidase to 5-15% of that caused by cisplatin, prevented loss of rat body weight, limited necrosis in the corticomedullary region to less than 1%, and did not counter cisplatin dependent tumor regression.

N-methyl-N-(2-sulfoethyl)-dithiocarbamate and N-methyl-N-(2-carboxyethyl)-dithiocarbamate gave equivalent kidney protection when administered at two- and four-fold higher doses, respectively. In contrast, use of DDTC using the same split-dose regimen at 90 mg/kg not only failed to protect the kidneys, but potentiated the cisplatin toxicity.

In addition, the PDC compounds of this invention are ideally suited for preparation of a kit containing both the cisplatin compound and the PDC compound of choice. Such a kit may comprise a carrier means being compartmentalized to receive in close confinement one or more container means such as vials, test tubes, and the like, each of said container means comprising one of the separate elements or dosage forms of the separate elements to be used in the method of treatment.

In this manner, one administering the cisplatin therapy need only proceed in accordance with the predetermined administration sequence, thereby eliminating uncertainty and potential error where materials in non-kit form, obtained from different sources, are required.

Referring now to the FIGURE, 10 is a kit comprising a rigid structural container having separate compartments 12 adapted for holding stoppered vials 14, 16, 18, and 20. Typically vial 14 contains an effective amount of a cisplatin compound while vials 16, 18 and 20 contain a polar dithiocarbamate compound according to the present invention. Each of the vials is sequentially numbered or otherwise identified to provide proper sequencing of administration.

While the FIGURE represents a preferred embodiment where the PDC is administered according to a split phase regimen, this is merely representative of the various modes contemplated and within the general scope of the invention.

Having now fully described the invention, it will be apparent to one with ordinary skill in the art that many changes and modifications can be made thereto without departing from the spirit or scope of the invention as set forth herein.

We claim as our invention the following:

1. A method for alleviating cisplatin-induced nephrotoxicity in an animal comprising administering to said animal an effective amount of a polar dithiocarbamate compound having the general formula:

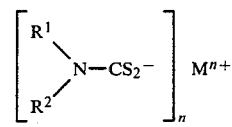

wherein $R^1$ and $R^2$ are aliphatic groups selected from the group consisting of branched or straight chain alkyl groups having 1-8 carbon atoms, alicyclic groups selected from the group consisting of cycloparaffins and partially hydrogenated aromatic compounds containing 3-8 carbon atoms, or aromatic groups containing at least 5-6 carbon atoms, or $R^1$ and $R^2$ taken together with the nitrogen form a heterocyclic ring containing 5 or 6 members and selected from the group consisting of pyrrole, pyrroline, pyrrolidine, pyridine, and piperidine, and either $R^1$, $R^2$, or both $R^1$ and $R^2$ contain a polar group selected from the group consisting of Cl, Br, I, F, $HSO_3$, $HCO_3$, $NO_2$, $NO_3$, $SO_3^-$, $CO_2^-$, $PO_3^{-2}$, $PO_2(OH)^-$, $PO_4^{-2}$, $PO_3(OH)^-$, $OR^3$, $N(R^3)_2$, and $CON(R^3)_2$, where $R^3$ is hydrogen, lower alkyl or alkyl substituted with polar groups, M is a pharmacologically acceptable cation, and n is an integer of 1-3;

said polar dithiocarbamate compound forming a platinum (II) complex having a water solubility of at least 0.2 micromoles per ml.

2. The method of claim 1 wherein said polar dithiocarbamate compound is sodium N-methyl-N-(2-sulfoethyl)-dithiocarbamate.

3. The method of claim 1 wherein said polar dithiocarbamate compound is sodium N-methyl-N-(2-carboxyethyl)-dithiocarbamate.

4. The method of claim 1 wherein said polar dithiocarbamate compound is sodium N,N-(2-hydroxyethyl)-dithiocarbamate.

5. A kit useful for alleviating cisplatin-induced nephrotoxicity comprising a carrier being compartmentalized to receive in close confinement therein more than one container wherein at least a first container contains an effective amount of cisplatin and at least a second container contains an effective amount of a polar dithiocarbamate compound having the general formula:

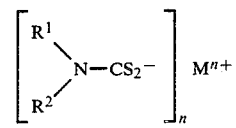

wherein $R^1$ and $R^2$ are aliphatic groups selected from the group consisting of branched or straight chain alkyl groups having 1-8 carbon atoms, alicyclic groups selected from the group consisting of cycloparaffins and partially hydrogenated aromatic compounds containing 3-8 carbon atoms, or aromatic groups containing at least 5-6 carbon atoms, or $R^1$ and $R^2$ taken together with the nitrogen form a heterocyclic ring containing 5 or 6 members and selected from the group consisting of pyrrole, pyrroline, pyrrolidine, pyridine, and piperidine, and either $R^1$, $R^2$, or both $R^1$ and $R^2$ contain a polar group selected from the group consisting of Cl, Br, I, F, $HSO_3$, $HCO_3$, $NO_2$, $NO_3$, $SO_3^-$, $CO_2^-$, $PO_3^{-2}$, $PO_2(OH)^-$, $PO_4^{-2}$, $PO_3(OH)^-$, $OR^3$, $N(R^3)_2$, and $CON(R^3)_2$, where $R^3$ is hydrogen, lower alkyl or alkyl substituted with polar groups, M is a pharmacologically acceptable cation, and n is an integer of 1-3;

said polar dithiocarbamate compound forming a platinum (II) complex having a water solubility of at least 0.2 micromoles per ml.

6. The method of claim 1 wherein said animal is man.

7. The method of claim 1 wherein said polar dithiocarbamate is administered parenterally.

8. The method of claim 1 wherein said polar dithiocarbamate is administered at a dosage level in the range of about 0.05 to 500 mg/kg.

9. The method of claim 1 wherein said polar dithiocarbamate is administered according to a split-dosage regimen.

10. Sodium N-methyl-N-(2-sulfoethyl)-dithiocarbamate.

* * * * *